United States Patent
AuCoin et al.

(10) Patent No.: US 9,279,808 B2
(45) Date of Patent: *Mar. 8, 2016

(54) METHOD OF DETECTING AND IDENTIFYING CIRCULATING ANTIGENS IN HUMAN BIOLOGICAL SAMPLES

(71) Applicants: David P. AuCoin, Reno, NV (US);
Thomas R. Kozel, Reno, NV (US);
Claire Smalley, Reno, NV (US)

(72) Inventors: David P. AuCoin, Reno, NV (US);
Thomas R. Kozel, Reno, NV (US);
Claire Smalley, Reno, NV (US)

(73) Assignee: Board of Regents of the Nevada System of Higher Education, on Behalf of the University of Nevada, Reno, Reno, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/573,933

(22) Filed: Dec. 17, 2014

(65) Prior Publication Data

US 2015/0132757 A1     May 14, 2015

Related U.S. Application Data

(62) Division of application No. 13/804,621, filed on Mar. 14, 2013, now Pat. No. 8,962,237.

(60) Provisional application No. 61/675,977, filed on Jul. 26, 2012.

(51) Int. Cl.
| | |
|---|---|
| *C12Q 1/00* | (2006.01) |
| *C12Q 1/68* | (2006.01) |
| *G01N 33/53* | (2006.01) |
| *G01N 33/554* | (2006.01) |
| *G01N 33/569* | (2006.01) |
| *C12Q 1/04* | (2006.01) |
| *G01N 33/536* | (2006.01) |

(52) U.S. Cl.
CPC ............ *G01N 33/56911* (2013.01); *C12Q 1/04* (2013.01); *G01N 33/536* (2013.01); *G01N 33/569* (2013.01)

(58) Field of Classification Search
CPC ................................................. G01N 33/56911
See application file for complete search history.

(56) References Cited

U.S. PATENT DOCUMENTS 8,962,237 B2 * 2/2015 AuCoin et al. ................... 435/4

OTHER PUBLICATIONS

AuCoin, "In vivo microbial antigen discovery: finding the 'needle in the haystack'," *Expert Rev. Mol. Diagn.*, vol. 12, No. 3, pp. 219-221 (2012).

Nuti et al., "Identification of Circulating Bacterial Antigens by In Vivo Microbial Antigen Discovery," *mBio*, vol. 2, Issue 4, pp. 1-8 (Jul./Aug. 2011).

\* cited by examiner

*Primary Examiner* — Albert Navarro
(74) *Attorney, Agent, or Firm* — Klarquist Sparkman, LLP (57) ABSTRACT

Disclosed herein is a method of detecting and identifying antigens that are shed into human bodily fluids during infection. The disclosed method allows circulating antigens associated with a particular infection to be detected within minutes or hours from testing as compared to days required with the current methods. Methods of identifying diagnostic indicators/targets for a given condition or disease are disclosed which include immunizing a verterinary subject with biological fluids obtained from a human infected with particular antigens to identify diagnostic targets for immunoassay. Also disclosed are methods of diagnosing and monitoring a *B. pseudomallei*-associated condition, such as melioidosis. Point-of-care immunoassays are also provided that can be used to diagnose or monitor the efficacy of a *B. pseudomallei*-associated condition treatment. These immunoassays can also be used for rapid diagnosis of infection produced by *B. pseudomallei*, such as meliodosis.

9 Claims, 2 Drawing Sheets

METHOD OF DETECTING AND IDENTIFYING CIRCULATING ANTIGENS IN HUMAN BIOLOGICAL SAMPLES

CROSS-REFERENCE TO RELATED APPLICATIONS

This application is a divisional of U.S. patent application Ser. No. 13/804,621, filed Mar. 14, 2013, which claims the benefit of priority under 35 U.S.C. §119 to U.S. Provisional Application No. 61/675,977, filed on Jul. 26, 2012, both of which are incorporated herein by reference in their entirety.

ACKNOWLEDGMENT OF GOVERNMENT SUPPORT

This invention was made with government support under Grant No. AI065359 awarded by the National Institutes of Health. The government has certain rights in the invention.

FIELD

This relates to the field of antigen detection and specifically to detecting and identifying antigens circulating in human biological samples.

BACKGROUND

Early diagnosis is critical for treatment of an infection to be effective. Diagnostic assays that are capable of detecting low levels of a particular molecule, such as an antigen, could greatly impact patient outcome because they would be able to detect the molecule and thus a condition associated with such within minutes or hours from testing as compared to days required with the current methods. Earlier detection translates into earlier administration of therapies which could significantly increase the likelihood of patient survival as well as decrease the severity of the disease.

Current diagnostic tools are limited and diagnosis with these methods often occurs when the infection is so severe that treatment is inefficient and ineffective. For example, diagnosing infections, such as bacterial and fungal infections, is often plagued by symptoms of the particular infection being non-specific making it difficult to obtain an accurate diagnosis at the onset of the disease. Current diagnostic assays often can only detect a particular molecule, such as an antigen, associated with a particular disease or condition if such molecule is present at high levels, thus only detecting the infection associated with the particular molecule not until the infection is well developed.

SUMMARY

Disclosed herein is a method of detecting and identifying antigens that are shed into human bodily fluids during infection. The disclosed method allows circulating antigens associated with a particular infection to be detected within minutes or hours from testing as compared to days required with the current methods. Earlier detection translates into earlier administration of therapies which increases the likelihood of patient survival as well as decreases the severity of the disease.

The disclosed method utilizes In vivo Microbial Antigen Discovery (InMAD). In contrast to studies previously utilizing InMAD which employed serum or urine from laboratory animals infected with a particular antigen to immunize a laboratory animal for identify circulating or secreted microbial antigens, the present method immunizes a laboratory animal with biological fluids obtained from a human infected with particular antigens to identify a diagnostic target for immunoassay. The inventors made the suprising discovery that biological samples collected from infected humans could be used to immunize a laboratory animal to identify circulating or secreted microbial antigens. One distinct advantage to the present method is that it controls for the possibility that the antigens associated with a particular infection in a verterinary subject model may not always correlate with that of a human. The human biological samples contain precisely the antigens that are targets for immunoassay for a given infection. Identification of the targets allows a diagnostic assay to be developed for a given condition in a human. It also allows for the effectiveness of a treatment for a given subject and/or group of subjects for a particular infection to be monitored.

In one embodiment of the InMAD technique, biological fluid samples, such as serum and urine samples, are collected from subjects afflicted with a given infection. Biological fluid samples are filtered to remove whole cells, but leave behind soluble antigens released during infection. The filtered samples are used to immunize naïve verterinary subjects and their serum is collected to identify antigens recognized by antibodies using one dimensional and two dimensional immunoblots prepared from whole cell lysates. Mass spectroscopy is used to identify those reactive antigens.

Based on these findings, disclosed herein are methods of identifying diagnostic indicators. In some embodiments, these methods include selecting a condition or disease for which a diagnostic assay is desired and is believed to be associated with one or more antigens; immunizing a verterinary subject which is not afflicted with the selected condition or disease with a human biological sample obtained from a human subject having the selected condition or disease; detecting one or more antigens in a biological sample obtained from the immunized animal subject; comparing the one or more antigens detected in the immunized animal subject sample with a control; and identifying one or more diagnostic indicators for the selected condition or disease, wherein an alteration in at least one antigen detected in the sample obtained from the immunized subject relative to the control indicates that such antigen is a diagnostic indicator for the condition or disease.

In some embodiments, the method further includes obtaining the biological sample, such as serum or urine, from the human subject with the selected condition or disease.

In some embodiments, the method further includes filtering the human biological sample obtained from the human subject to isolate the one or more soluble antigens.

In some embodiments, the method further includes obtaining the biological sample, such as serum or urine, from the immunized animal subject prior to detecting one or more antigens.

In some embodiments of the method, detecting one or more antigens in a biological sample obtained from the immunized animal subject includes using one-dimensional or two-dimensional immunoblots followed by mass spectroscopy to identify the one or more antigens.

Also disclosed are methods of diagnosing and monitoring an antigen-associated condition, such as *Burkholderia pseudomallei*-associated condition including melioidosis. In one example, the disclosed methods allow for self monitoring in which a subject, such as an immunosuppressed patient, monitors the presence of one or more specific antigens, to monitor the onset of an infection.

The foregoing and other features will become more apparent from the following detailed description of several embodiments, which proceeds with reference to the accompanying figures.

BRIEF DESCRIPTION OF THE FIGURES

FIG. 2B is digital image of a two-dimensional Western blot of *B. pseudomallei* lysate probed with InMAD immune serum from 
includes a protein with modifications, such as deletions, additions and substitutions (generally conservative in nature) to the native sequence, so long as the protein maintains the ability to elicit an immunological response, as defined herein. These modifications may be deliberate, as through site-directed mutagenesis, or may be accidental, such as through mutations of hosts which produce the antigens.

Bacteria: A large domain of prokaryotic microorganisms. Typically a few micrometres in length, bacteria have a wide range of shapes, ranging from spheres to rods and spirals. There are broadly speaking two different types of cell wall in bacteria, called Gram-positive and Gram-negative. Gram-positive bacteria possess a thick cell wall containing many layers of peptidoglycan and teichoic acids. In contrast, Gram-negative bacteria have a relatively thin cell wall consisting of a few layers of peptidoglycan surrounded by a second lipid membrane containing lipopolysaccharides and lipoproteins. Most bacteria have the Gram-negative cell wall, and only the Firmicutes and Actinobacteria have the alternative Gram-positive arrangement. An example of a Gram-negative bacterium is *Burkholderia pseudomallei*. A "*Burkholderia pseudomallei*-associated molecule" is a molecule associated with one or more signs or symptoms of melioidosis. In some examples, a melioidosis-associated molecule is one or more of the antigens provided in Table 1.

Contacting: "Contacting" includes in solution and solid phase, for example contacting a salivary protein with a test agent. The test agent may also be a combinatorial library for screening a plurality of compounds. In another example, contacting includes contacting a sample with an antibody, for example contacting a sample that contains a protein of interest such as a protein associated with a particular condition or disease.

Diagnosis: The process of identifying a condition or disease by its signs, symptoms, results of various tests and presence of diagnostic indicators. The conclusion reached through that process is also called "a diagnosis."

Electron Transfer flavoprotein subunit alpha (ETFA): The alpha subunit of the electron transfer flavoprotein (ETF). ETFs are heterodimeric proteins composed of an alpha and beta subunit (ETFA and ETFB), and contain an FAD cofactor and AMP. ETF has three domains: domains I and II are formed by the N- and C-terminal portions of the alpha subunit, respectively, while domain III is formed by the beta subunit.

ETFA is encoded by the ETFA gene. ETFA participates in catalyzing the initial step of the mitochondrial fatty acid beta oxidation. It shuttles electrons between primary flavoprotein dehydrogenases and the membrane-bound electron transfer flavoprotein ubiquinone oxidoreductase. Defects in electron-transfer-flavoprotein have been implicated in type II glutaricaciduria in which multiple acyl CoA dehydrogenase deficiencies result in large excretion of glutaric, lactic, ethylmalonic, butyric, isobutyric, 2-methyl-butyric, and isovaleric acids. ETFA is detected in a subject with *B. pseudomallei* and can be used to diagnosis or monitor such condition.

Exemplary nucleic acid and protein sequences for ETFA are publicly available (see, Entrez No. 2108 or GenBank No. NM_000126.3 for human ETFA nucleic acid sequences; Entrez No. 110842 or GenBank No. NM_145615.4 for mouse ETFA nucleic acid sequences; and GenBank Nos. NP_000117.1 (human) and NP_663590.3 (mouse) for ETFA protein sequences; each of which hereby incorporated by reference as available on Jul. 26, 2012).

In one example, ETFA includes a full-length wild-type (or native) sequence, as well as ETFA allelic variants, fragments, homologs or fusion sequences that retain the ability to be detected in a subject with melioidosis. In certain examples, ETFA has at least 80% sequence identity, for example at least 85%, 90%, 95%, or 98% sequence identity to a known ETFA and retains ETFA activity (e.g., the capability to be detected in a subject with melioidosis). ETFA is detected in a subject with *B. pseudomallei* and can be used to diagnosis or monitor such condition.

FtsA/FtsZ: FtsA is a protein encoded by the FtsA gene and participates in formation of the *Escherichia coli* septum structure. FtsZ is a protein encoded by the ftsZ gene that assembles into a ring at the future site of the septum of bacterial cell division. FtsA and FtsZ are involved in cell divisiona. FtsA/FtsZ has been named after "Filamenting temperature-sensitive mutant A" whereas FtsZ is for "Filamenting temperature-sensitive mutant Z."

Exemplary nucleic acid and protein sequences for FtsA/FTsZ are publicly available (see, GenBank Nos. gi 53720630/53720631, each of which hereby incorporated by reference as available on Jul. 26, 2012).

In one example, FtsA/FtsZ includes a full-length wild-type (or native) sequence, as well as FtsA/FtsZ allelic variants, fragments, homologs or fusion sequences that retain the ability to be detected in a subject with melioidosis. In certain examples, FtsA/FtsZ has at least 80% sequence identity, for example at least 85%, 90%, 95%, or 98% sequence identity to a known FtsA/FtsZ and retains FtsA/FtsZ activity (e.g., the capability to be detected in a subject with melioidosis). FtsA/FtsZ are detected in a subject with *B. pseudomallei* and can be used to diagnosis or monitor such condition.

Fungus: Living, single-celled and multicellular organisms belonging to the kingdom Fungi. Most species are characterized by a lack of chlorophyll and presence of chitinous cell walls, and some fungi may be multinucleated. The methods disclosed herein can be used to detect and identify antigens associated with particular fungi. In one example, the method is used to detect a fungus, such as an *Aspergillus* species. Representative, non-limiting examples of *Aspergillus* species include *A. candidus, A. chevalieri, A. clavatus, A. flavipes, A. flavus, A. fumigatus, A. granulosus, A. nidulans, A. niger, A. parasiticus, A. restrictus, A. sydowii, A. tamari, A. ustus, A. versicolor*, and *A. wentii.*

GroEL: A protein that belongs to the alkalai family of molecular chaperones, and is found in a large number of bacteria. It is known to play a role in protein folding. To function properly, GroEL requires the lid-like co-chaperonin protein complex GroES. In eukaryotes, the protein Hsp60 is believed to be structurally and functionally nearly identical to GroEL.

Exemplary nucleic acid and protein sequences for GroEL are publicly available (see, GenBank Nos. NM_002156 (human) and NM_010477 (mouse) for GroEL nucleic acid sequences and NP_002147 (human) and NP_034607 (mouse) for GroEL protein sequences; each of which hereby incorporated by reference as available on Jul. 26, 2012).

In one example, GroEL includes a full-length wild-type (or native) sequence, as well as GroEL allelic variants, fragments, homologs or fusion sequences that retain the ability to be detected in a subject with melioidosis. In certain examples, GroEL has at least 80% sequence identity, for example at least 85%, 90%, 95%, or 98% sequence identity to a known GroEL and retains GroEL activity (e.g., the capability to be detected in a subject with melioidosis).

Glutathione S-transferase (GST) domain containing protein: A structural domain of glutathione S-transferase (GST). GST conjugates reduced glutathione to a variety of targets including S-crystallin from squid, the eukaryotic elongation factor 1-gamma, the HSP26 family of stress-related proteins and auxin-regulated proteins in plants. The glutathione molecule binds in a cleft between N and C-terminal domains. The catalytic residues are proposed to reside in the N-terminal domain. In eukaryotes, glutathione S-transferases (GSTs) participate in the detoxification of reactive electrophilic compounds by catalysing their conjugation to glutathione. The GST domain is also found in S-crystallins from squid and proteins with no known GST activity, such as eukaryotic elongation factors 1-gamma and the HSP26 family of stress-related proteins, which include auxin-regulated proteins in plants and stringent starvation proteins in *Escherichia coli*. Bacterial GSTs of known function often have a specific, growth-supporting role in biodegradative metabolism: epoxide ring opening and tetrachlorohydroquinone reductive dehalogenation are two examples of the reactions catalysed by these bacterial GSTs. Some regulatory proteins, like the stringent starvation proteins, also belong to the GST family. Glutathione S-transferases form homodimers, but in eukaryotes can also form heterodimers of the A1 and A2 or YC1 and YC2 subunits. The homodimeric enzymes display a conserved structural fold. Each monomer is composed of a distinct N-terminal sub-domain, which adopts the thioredoxin fold, and a C-terminal all-helical sub-domain. This entry is the C-terminal domain.

Exemplary protein sequences for glutathione S-transferase domain containing protein are publicly available (see, GenBank No. gi 76808775, which hereby incorporated by reference as available on Jul. 26, 2012).

In one example, GST domain containing protein includes a full-length wild-type (or native) sequence, as well as GST domain containing protein allelic variants, fragments, homologs or fusion sequences that retain the ability to be detected in a subject with melioidosis. In certain examples, GST dom 
viruses and prions (which are generally classified as non-living). Microorganisms that cause disease in a host are known as pathogens.

Transcription Elongation Factor NusA: A protein associated with *B. pseudomallei* and can be used to diagnosis or monitor a *B. pseudomallei* infection such as melioidosis. Exemplary nucleic acid and protein sequences for transcription elongation factor NusA are publicly available (see, for example, GenBank Nos. EIM96869.1, AEW69130.1, YP_542577.1, and ZP_10253383.1 for exemplary protein sequences, each of which hereby incorporated by reference as available on Jul. 26, 2012).

In one example, transcription elongation factor NusA includes a full-length wild-type (or native) sequence, as well as transcription elongation factor NusA allelic variants, fragments, homologs or fusion sequences that retain the ability to be detected in a subject with melioidosis. In certain examples, transcription elongation factor NusA has at least 80% sequence identity, for example at least 85%, 90%, 95%, or 98% sequence identity to a known transcription elongation factor NusA and retains transcription elongation factor NusA activity (e.g., the capability to be detected in a subject with melioidosis). Transcription elongation factor NusA is detected in a subject with *B. pseudomallei* and can be used to diagnosis or monitor such condition.

II. Methods for Detecting and Identifying Circulating Antigens

Disclosed herein are methods for detecting and identifying circulating antigens that can be used to identify diagnostic indicators/targets of specific conditions and/or diseases. In one example, a method of identifying one or more diagnostic indicators includes selecting a condition or disease for which a diagnostic assay is desired and is believed to be associated with one or more antigens. For example, the condition can be one that is associated with a particular set of clinical factors/symptoms or presence of a microorganism such a fungus or bacteria.

The method for identifying one or more diagnostic indicators also includes immunizing a verterinary subject (such as a mouse or rabbit) that is not afflicted with the selected condition or disease with a human biological sample obtained from a human subject having the selected condition or disease. For example, a biological sample, such as urine, is collected from a human subject displaying one or more signs or symptoms associated with the selected condition or disease for which a diagnostic assay is desired. In other examples, other biological fluids, such as blood (such as whole blood obtained from a finger prick), GCF, amniotic fluid, BALF, salvia or tears are collected. In some embodiments, the method further includes filtering the human biological sample obtained from the human subject to isolate the one or more soluble antigens present in the sample.

The disclosed method for identifying one or more diagnostic indicators/targets also includes detecting one or more antigens in a biological sample obtained from the immunized animal subject; comparing the one or more antigens detected in the immunized animal subject sample with a control; and identifying one or more diagnostic indicators for the selected condition or disease, wherein an alteration in at least one antigen detected in the sample obtained from the immunized subject relative to the control indicates that such antigen is a diagnostic indicator for the condition or disease. In some examples, the method further includes obtaining the biological sample, such as serum or urine, from the immunized animal subject prior to detecting one or more antigens. In some embodiments of the method, detecting one or more antigens in a biological sample obtained from the immunized animal subject includes using one-dimensional or two-dimensional immunoblots followed by mass spectroscopy to identify the one or more antigens.

In some examples, the method includes detecting an increase, such as a statistically significant increase, such as an at least a 1.5, 2, 3, 4, or 5 fold increase in the amount of one or more molecules associated with condition or disease, including at least a 1.5, 2, 3, 4, or 5 fold increase to a control or reference value, such as between a 1.5 to 5 fold increase, a 2 to 6 fold increase, a 3 to 10 fold increase, including a 2 fold, a 3 fold, a 4 fold, a 5 fold, a 6 fold, a 7 fold, a 8 fold, a 9 fold or 10 fold increase. In some embodiments, the method includes detecting a decrease, such as a statistically significant decrease, such as at least a 2, 3, 4, or 5 fold decrease in the amount of one or more molecules associated with the selected condition or disease, such as one or more protein antigens, as compared to a control or reference sample, such as between a 1.5 to 5 fold decrease, a 2 to 6 fold decrease, a 3 to 10 fold decrease, including a 2 fold, a 3 fold, a 4 fold, a 5 fold, a 6 fold, a 7 fold, a 8 fold, a 9 fold or 10 fold decrease.

In some embodiments of the method, the disclosed methods allow for self monitoring in which a subject, such as an immuno suppressed patient, monitors the presence of one or more specific antigens, to monitor the onset of an infection.

III. Methods for Detecting *B. pseudomallei*-Associated Condition and Monitoring the Efficacy of a Therapeutic Regimen Methods are disclosed herein that are of use to determine if a subject has a *B. pseudomallei*-associated condition, such as melioidosis, including acute or chronic melioidosis, or to monitor the efficacy of therapy. These methods utilize a biological fluid, such as, but not limited to urine or serum, for the detection of a molecule associated *B. pseudomallei*, such as melioidosis, including, but not limited to, protein antigens listed in Table 1. The *B. pseudomallei*-associated molecules, such as melioidosis-associated molecules, include any naturally occurring forms of the proteins, such as but not limited to glycosylated forms. In some embodiments, the methods disclosed herein are used to identify a subject as having acute melioidosis. In other embodiments, the methods are used to identify chronic melioidosis. In even further embodiments, the methods are used to diagnosis latent melioidosis. These methods can be performed over time, to monitor the progression or regression of melioidosis in a subject, or to assess for the development of melioidosis from a pre-melioidosis condition. In some examples, the disclosed methods are used for self monitoring in which a subject, such as an immunosuppressed human subject, monitors the presence of one or more molecules associated with *B. pseudomallei*, such as melioidosis, to monitor the onset of an infection. In additional examples, the disclosed methods and kits are used for self monitoring in which a subject, such as a subject that has previously been diagnosed and treated for a melioidosis associated condition or disease practices the method or uses the kit to monitor for relapse.

Methods are disclosed herein that include testing a biological sample, such as a serum or urine sample, obtained from a human at risk or suspected of having melioidosis. In one example, the biological sample is a biological fluid, such as urine. However, other biological fluids are also of use, such as blood (such as whole blood obtained from a finger prick), GCF, amniotic fluid, BALF, *salvia* or tears. The methods include detecting, or determining the abundance (amount) of one or more molecules associated with melioidosis, including protein antigens listed in Table 1. In some examples, the methods include determining a proteomic profile.

In one example, the method includes detecting at least GroEL. In one example, the method includes detecting GroEL and at least one more molecule associated with melioidosis such as one or more molecules listed in Table 1. The methods can include detecting at least one, such as at least two, at least three, at least four, at least five, at least six, at least seven, at least eight, at least nine, at least ten, at least eleven, at least twelve, including one, two, three, four, five, six, seven, eight, nine, ten, eleven, or twelve molecules associated with melioidosis. In one example, the method includes detecting at least one, at least two, at least three, at least four, at least five, at least six, at least seven, at least eight, at least nine, at least ten, at least eleven, at least twelve, including one, two, three, four, five, six, seven, eight, nine, ten, eleven, or twelve molecules listed in Table 1.

In some embodiments, the method includes detecting an increase, such as a statistically significant increase, such as an at least a 1.5, 2, 3, 4, or 5 fold increase in the amount of one or more molecules associated with melioidosis, including at least a 1.5, 2, 3, 4, or 5 fold increase in one or more protein antigens listed in Table 1 as compared to a reference value. In some embodiments, the method includes detecting a decrease, such as a statistically significant decrease, such as at least a 2, 3, 4, or 5 fold decrease in the amount of one or more protein antigens listed in Table 1 as compared to a reference sample.

In one embodiment, the method includes comparing a proteomic profile of a test sample of urine from a human subject of interest comprising at least one of protein associated with melioidosis, such a protein antigen listed in Table 1, with a proteomic profile from a reference sample.

In one embodiment, the method determines if the human subject has melioidosis. If the reference sample is a normal sample and the proteomic profile of the test sample is essentially the same as the proteomic profile of the normal sample, the human subject is determined not to have melioidosis. However, if the proteomic profile of the test sample has a unique expression signature relative to the proteomic profile of the normal sample the human subject is determined to have melioidosis.

In some embodiments, if the reference sample is a sample from a human subject with melioidosis, and its proteomic profile shares at least one unique expression signature characteristic with the reference sample, then the human subject is determined to have melioidosis. If the proteomic profile of the test sample has a unique expression signature relative to the reference sample the human subject is determined not to have melioidosis. Hence, the proteomic profile provides an additional diagnostic criterion for these disorders.

In one embodiment, the method is a method to determine if a therapy is effective for the treatment of the human subject by detecting the presence of at least one protein associated with melioidosis. The method can be performed multiple times over a specified time period, such as days, weeks, months or years. In several examples, the therapy includes treatment with a therapeutic agent for melioidosis. If the reference sample is a normal human sample, and the proteomic profile of the test sample is essentially the same as the proteomic profile of the normal sample the human subject is determined to have an effective therapy, while if the proteomic profile of the test sample has a unique expression signature relative to the proteomic profile of the normal sample to have an ineffective therapy. If the reference sample is a sample from a human subject with melioidosis, and proteomic profile shares at least one unique expression signature characteristic with the reference sample then the human subject is determined to have an ineffective therapy, while if the proteomic profile of the test sample has a unique expression signature relative to the reference sample the human subject is determined to have an effective therapy. Changes in the profile can also represent the progression (or regression) of the disease process. Methods for monitoring the efficacy of therapeutic agents are described below.

Monitoring

The diagnostic methods of the present disclosure are valuable tools for practicing physicians to make quick treatment decisions for melioidosis conditions, including both acute and chronic melioidosis. These treatment decisions can include the administration of an anti-melioidosis agent and decisions to monitor a subject for onset and/or advancement of melioidosis. The method disclosed herein can also be used to monitor the effectiveness of a therapy.

Following the measurement of the expression levels of one or more of the molecules identified herein, the assay results, findings, diagnoses, predictions and/or treatment recommendations are typically recorded and communicated to technicians, physicians and/or patients, for example. In certain embodiments, computers will be used to communicate such information to interested parties, such as, patients and/or the attending physicians. Based on the measurement, the therapy administered to a subject can be modified.

In one embodiment, a diagnosis, prediction and/or treatment recommendation based on the expression level in a test subject of one or more of the melioidosis associated molecules disclosed herein is communicated to the subject as soon as possible after the assay is completed and the diagnosis and/or prediction is generated. The results and/or related information may be communicated to the subject by the subject's treating physician. Alternatively, the results may be communicated directly to a test subject by any means of communication, including writing, such as by providing a written report, electronic forms of communication, such as email, or telephone. Communication may be facilitated by use of a computer, such as in case of email communications. In certain embodiments, the communication containing results of a diagnostic test and/or conclusions drawn from and/or treatment recommendations based on the test, may be generated and delivered automatically to the subject using a combination of computer hardware and software which will be familiar to artisans skilled in telecommunications. One example of a healthcare-oriented communications system is described in U.S. Pat. No. 6,283,761; however, the present disclosure is not limited to methods which utilize this particular communications system. In certain embodiments of the methods of the disclosure, all or some of the method steps, including the assaying of samples, diagnosing of diseases, and communicating of assay results or diagnoses, may be carried out in diverse (e.g., foreign) jurisdictions.

In several embodiments, identification of a subject as having melioidosis results in the physician treating the subject, such as prescribing one or more therapeutic agents for inhibiting or delaying one or more signs and symptoms associated with melioidosis. In additional embodiments, the dose or dosing regimen is modified based on the information obtained using the methods disclosed herein.

The subject can be monitored while undergoing treatment using the methods described herein in order to assess the efficacy of the treatment protocol. In this manner, the length of time or the amount give to the subject can be modified based on the results obtained using the methods disclosed herein.

IV. Immunoassays for Diagnosing and Monitoring *B. pseudomallei*-associated Conditions The methods disclosed herein can be performed in the form of various immunoassay formats, which are well known in the art. There are two main types of immunoassays, homoge- neous and heterogeneous. In homogeneous immunoassays, both the immunological reaction between an antigen and an antibody and the detection are carried out in a homogeneous reaction. Heterogeneous immunoassays include at least one separation step, which allows the differentiation of reaction products from unreacted reagents. A variety of immunoassays can be used to detect one or more of the molecules capable of detecting a B. pseudomallei-associated molecule, including detecting extracellular polysaccharides. In one example, one or more antigens associated with an *B. pseudomallei*-associated disorder/condition are measured to diagnose an *B. pseudomallei*-associated disorder, such as melioidosis. For example, one or more antigens listed in Table 1 are detected with a disclosed immunoassay. In some examples, the disclosed immunoassay includes at least one, such as two, three, four, five, six, seven, eight, nine, ten, eleven, or more molecules associated with a *B. pseudomallei*-associated condition or disease, such as melioidosis. In one example, the immunoassay includes at least one, such as two, three, four, five, six, seven, eight, nine, ten, or eleven molecules listed in Table 1.

ELISA is a heterogeneous immunoassay, which has been widely used in laboratory practice since the early 1970s, and can be used in the methods disclosed herein. The assay can be used to detect protein antigens in various formats. In the "sandwich" format the antigen being assayed is held between two different antibodies. In this method, a solid surface is first coated with a solid phase antibody. The test sample, containing the antigen (e.g., a diagnostic protein), or a composition containing the antigen, such as a urine sample from a subject of interest, is then added and the antigen is allowed to react with the bound antibody. Any unbound antigen is washed away. A known amount of enzyme-labeled antibody is then allowed to react with the bound antigen. Any excess unbound enzyme-linked antibody is washed away after the reaction. The substrate for the enzyme used in the assay is then added and the reaction between the substrate and the enzyme produces a color change. The amount of visual color change is a direct measurement of specific enzyme-conjugated bound antibody, and consequently the antigen present in the sample tested.

ELISA can also be used as a competitive assay. In the competitive assay format, the test specimen containing the antigen to be determined is mixed with a precise amount of enzyme-labeled antigen and both compete for binding to an anti-antigen antibody attached to a solid surface. Excess free enzyme-labeled antigen is washed off before the substrate for the enzyme is added. The amount of color intensity resulting from the enzyme-substrate interaction is a measure of the amount of antigen in the sample tested. A heterogeneous immunoassay, such as an ELISA, can be used to detect any molecules associated with a *B. pseudomallei* antigen.

In another example, immuno-PCR can be used to detect any of the molecules associated with a *B. pseudomallei* condition such as melioidosis. Immuno-PCR is a modification of the conventional ELISA format in which the detecting antibody is labeled with a DNA label, and is applicable to the analysis of biological samples (see, e.g., U.S. Pat. No. 5,665,539 and U.S. Patent Application Publication No. 2005/0239108; all herein incorporated by reference). The amplification ability of PCR provides large amounts of the DNA label which can be detected by various methods, typically gel electrophoresis with conventional staining (e.g., Sano et al., Science, 258:120-122, 1992). This method can also include the direct conjugation of the DNA label to the antibody and replacement of gel electrophoresis by using labeled primers to generate a PCR product that can be assayed by ELISA or using real time quantitative PCR. In an example of the real-time PCR method, PCR is used to amplify DNA in a sample in the presence of a nonextendable dual labeled fluorogenic hybridization probe. One fluorescent dye serves as a reporter and its emission spectra is quenched by the second fluorescent dye. The method uses the 5' nuclease activity of Taq polymerase to cleave a hybridization probe during the extension phase of PCR. The nuclease degradation of the hybridization probe releases the quenching of the reporter dye resulting in an increase in peak emission from the reporter. The reactions are monitored in real time.

Homogeneous immunoassays include, for example, the Enzyme Multiplied Immunoassay Technique (EMIT), which typically includes a biological sample comprising the biomarkers to be measured, enzyme-labeled molecules of the biomarkers to be measured, specific antibody or antibodies binding the biomarkers to be measured, and a specific enzyme chromogenic substrate. In a typical EMIT, excess of specific antibodies is added to a biological sample. If the biological sample contains the molecules to be detected, such molecules bind to the antibodies. A measured amount of the corresponding enzyme-labeled molecules is then added to the mixture. Antibody binding sites not occupied by molecules of the protein in the sample are occupied with molecules of the added enzyme-labeled protein. As a result, enzyme activity is reduced because only free enzyme-labeled protein can act on the substrate. The amount of substrate converted from a colorless to a colored form determines the amount of free enzyme left in the mixture. A high concentration of the protein to be detected in the sample causes higher absorbance readings. Less protein in the sample results in less enzyme activity and consequently lower absorbance readings. Inactivation of the enzyme label when the antigen-enzyme complex is antibody-bound makes the EMIT a useful system, enabling the test to be performed without a separation of bound from unbound compounds as is necessary with other immunoassay methods. A homogenous immunoassay, such as an EMIT, can be used to detect any of the molecules associated with a *B. pseudomallei*-associated condition or disease, such as *B. pseudomallei* protein antigens listed in Table 1.

Immunoassay kits are also disclosed herein. These kits include, in separate containers (a) monoclonal antibodies having binding specificity for the polypeptides used in the diagnosis of an *B. pseudomallei*-associated condition/disorder, such as melioidosis; and (b) and anti-antibody immunoglobulins. This immunoassay kit may be utilized for the practice of the various methods provided herein. The monoclonal antibodies and the anti-antibody immunoglobulins can be provided in an amount of about 0.001 mg to 100 grams, and more preferably about 0.01 mg to 1 gram. The anti-antibody immunoglobulin may also be a polyclonal immunoglobulin, protein A or protein G or functional fragments thereof, which may be labeled prior to use by methods known in the art. In several embodiments, the immunoassay kit includes one, two, three or four or more antibodies that specifically bind to molecules associated with a *B. pseudomallei*-associated condition or disease, such as *B. pseudomallei* protein antigens listed in Table 1. The immunoassay kit can also include one or more antibodies that specifically bind to one or more of these molecules. Thus, the kits can be used to detect one or more different molecules associated an *B. pseudomallei*-associated condition, such as melioidosis.

Immunoassays for polysaccharides and proteins differ in that a single antibody is used for both the capture and indicator roles for polysaccharides due to the presence of repeating epitopes. In contrast, two antibodies specific for distinct epitopes are required for immunoassay of proteins. Exemplary samples include biological samples obtained from subjects including, but not limited to, serum, blood and urine samples. In some examples, an exemplary sample includes bronchoalveolar lavage fluid.

In one particular example, a quantitative ELISA is constructed for detection of at least one of the *B. pseudomallei* protein antigens listed in Table 1. These immunoassays utilize antibodies, such as mAbs commercially available. Since a polysaccharide is a polyvalent repeating structure, a single mAb may be used for both the capture and indicator phases of an immunoassay. The only requirement is that the mAb have a sufficient affinity. A mAb with an affinity of about 0.5 μM has sufficient affinity.

V. Capture Device Methods

The disclosed methods can be carried out using a sample capture device, such as a lateral flow device (for example a lateral flow test strip) that allows detection of one or more molecules, such as those described herein.

Point-of-use analytical tests have been developed for the routine identification or monitoring of health-related conditions (such as pregnancy, cancer, endocrine disorders, infectious diseases or drug abuse) using a variety of biological samples (such as urine, serum, plasma, blood, saliva). Some of the point-of-use assays are based on highly specific interactions between specific binding pairs, such as antigen/antibody, hapten/antibody, lectin/carbohydrate, apoprotein/cofactor and biotin/(strept)avidin. The assays are often performed with test strips in which a specific binding pair member is attached to a mobilizable material (such as a metal sol or beads made of latex or glass) or an immobile substrate (such as glass fibers, cellulose strips or nitrocellulose membranes). Particular examples of some of these assays are shown in U.S. Pat. Nos. 4,703,017; 4,743,560; and 5,073,484 (incorporated herein by reference). The test strips include a flow path from an upstream sample application area to a test site. For example, the flow path can be from a sample application area through a mobilization zone to a capture zone. The mobilization zone may contain a mobilizable marker that interacts with an analyte or analyte analog, and the capture zone contains a reagent that binds the analyte or analyte analog to detect the presence of an analyte in the sample.

Examples of migration assay devices, which usually incorporate within them reagents that have been attached to colored labels, thereby permitting visible detection of the assay results without addition of further substances are found, for example, in U.S. Pat. No. 4,770,853; WO 88/08534; and EP-A 0 299 428 (incorporated herein by reference). There are a number of commercially available lateral-flow type tests and patents disclosing methods for the detection of large analytes (MW greater than 1,000 Daltons) as the analyte flows through multiple zones on a test strip. Examples are found in U.S. Pat. No. 5,229,073 (measuring plasma lipoprotein levels), and U.S. Pat. Nos. 5,591,645; 4,168,146; 4,366,241; 4,855,240; 4,861,711; 5,120,643; European Patent No. 0296724; WO 97/06439; WO 98/36278; and WO 08/030546 (each of which are herein incorporated by reference). Multiple zone lateral flow test strips are disclosed in U.S. Pat. No. 5,451,504, U.S. Pat. No. 5,451,507, and U.S. Pat. No. 5,798,273 (incorporated by reference herein). U.S. Pat. No. 6,656,744 (incorporated by reference) discloses a lateral flow test strip in which a label binds to an antibody through a streptavidin-biotin interaction.

In particular examples, the methods disclosed herein include application of a biological sample (such as serum, whole blood or urine) from a human test subject to a lateral flow test device for the detection of one or more molecules (such as one or more molecules associated with melioidosis, for example, combinations of molecules as described above) in the sample. The lateral flow test device includes one or more antibodies (such as antibodies that bind one or more of the molecules associated with melioidosis) at an addressable location. In a particular example, the lateral flow test device includes antibodies that bind at least one melioidosis protein antigen listed in Table 1. The addressable locations can be, for example, a linear array or other geometric pattern that provides diagnostic information to the user. The binding of one or more molecules in the sample to the antibodies present in the test device is detected and the presence or amount of one or more molecules in the sample of the test subject is compared to a control, wherein a change in the presence or amount of one or more molecules in the sample from the test subject as compared to the control indicates that the subject has a *B. pseudomallei* associated condition, such as melioidosis.

Devices described herein generally include a strip of absorbent material (such as a microporous membrane), which, in some instances, can be made of different substances each joined to the other in zones, which may be abutted and/or overlapped. In some examples, the absorbent strip can be fixed on a supporting non-interactive material (such as nonwoven polyester), for example, to provide increased rigidity to the strip. Zones within each strip may differentially contain the specific binding partner(s) and/or other reagents required for the detection and/or quantification of the particular analyte being tested for, for example, one or more molecules disclosed herein. Thus these zones can be viewed as functional sectors or functional regions within the test device.

In general, a fluid sample is introduced to the strip at the proximal end of the strip, for instance by dipping or spotting. A sample is collected or obtained using methods well known to those skilled in the art. The sample containing the particular molecules to be detected may be obtained from any biological source. Examples of biological sources include blood serum, blood plasma, urine, BALF, spinal fluid, saliva, fermentation fluid, lymph fluid, tissue culture fluid and ascites fluid of a human or animal. In a particular example, the biological source is saliva. In one particular example, the biological source is whole blood, such as a sample obtained from a finger prick. The sample may be diluted, purified, concentrated, filtered, dissolved, suspended or otherwise manipulated prior to assay to optimize the immunoassay results. The fluid migrates distally through all the functional regions of the strip. The final distribution of the fluid in the individual functional regions depends on the adsorptive capacity and the dimensions of the materials used.

Another common feature to be considered in the use of assay devices is a means to detect the formation of a complex between an analyte (such as one or more molecules described herein) and a capture reagent (such as one or more antibodies). A detector (also referred to as detector reagent) serves this purpose. A detector may be integrated into an assay device (for example included in a conjugate pad, as described below), or may be applied to the device from an external source.

A detector may be a single reagent or a series of reagents that collectively serve the detection purpose. In some instances, a detector reagent is a labeled binding partner specific for the analyte (such as a gold-conjugated antibody for a particular protein of interest, for example those described herein).

In other instances, a detector reagent collectively includes an unlabeled first binding partner specific for the analyte and a labeled second binding partner specific for the first binding partner and so forth. Thus, the detector can be a labeled antibody specific for a protein described herein. The detector can also be an unlabeled first antibody specific for the protein of interest and a labeled second antibody that specifically binds the unlabeled first antibody. In each instance, a detector reagent specifically detects bound analyte of an analyte-capture reagent complex and, therefore, a detector reagent preferably does not substantially bind to or react with the capture reagent or other components localized in the analyte capture area. Such non-specific binding or reaction of a detector may provide a false positive result. Optionally, a detector reagent can specifically recognize a positive control molecule (such as a non-specific human IgG for a labeled Protein A detector, or a labeled Protein G detector, or a labeled anti-human Ab(Fc)) that is present in a secondary capture area.

Flow-Through Device Construction and Design

Representative flow-through assay devices are described in U.S. Pat. Nos. 4,246,339; 4,277,560; 4,632,901; 4,812,293; 4,920,046; and 5,279,935; U.S. Patent Application Publication Nos. 20030049857 and 20040241876; and WO 08/030546. A flow-through device involves a capture reagent (such as one or more antibodies) immobilized on a solid support, typically, a membrane (such as, nitrocellulose, nylon, or PVDF). Characteristics of useful membranes have been previously described; however, it is useful to note that in a flow-through assay capillary rise is not a particularly important feature of a membrane as the sample moves vertically through the membrane rather than across it as in a lateral flow assay. In a simple representative format, the membrane of a flow-through device is placed in functional or physical contact with an absorbent layer (see, e.g., description of "absorbent pad" below), which acts as a reservoir to draw a fluid sample through the membrane. Optionally, following immobilization of a capture reagent, any remaining protein-binding sites on the membrane can be blocked (either before or concurrent with sample administration) to minimize nonspecific interactions.

In operation of a flow-through device, a fluid sample (such as a bodily fluid sample) is placed in contact with the membrane. Typically, a flow-through device also includes a sample application area (or reservoir) to receive and temporarily retain a fluid sample of a desired volume. The sample passes through the membrane matrix. In this process, an analyte in the sample (such as one or more protein, for example, one or more molecules described herein) can specifically bind to the immobilized capture reagent (such as one or more antibodies). Where detection of an analyte-capture reagent complex is desired, a detector reagent (such as labeled antibodies that specifically bind one or more molecules) can be added with the sample or a solution containing a detector reagent can be added subsequent to application of the sample. If an analyte is specifically bound by capture reagent, a visual representative attributable to the particular detector reagent can be observed on the surface of the membrane. Optional wash steps can be added at any time in the process, for instance, following application of the sample, and/or following application of a detector reagent.

Lateral Flow Device Construction and Design

Lateral flow devices are commonly known in the art. Briefly, a lateral flow device is an analytical device having as its essence a test strip, through which flows a test sample fluid that is suspected of containing an analyte of interest. The test fluid and any suspended analyte can flow along the strip to a detection zone in which the analyte (if present) interacts with a capture agent and a detection agent to indicate a presence, absence and/or quantity of the analyte.

Numerous lateral flow analytical devices have been disclosed, and include those shown in U.S. Pat. Nos. 4,168,146; 4,313,734; 4,366,241; 4,435,504; 4,775,636; 4,703,017; 4,740,468; 4,806,311; 4,806,312; 4,861,711; 4,855,240; 4,857,453; 4,861,711; 4,943,522; 4,945,042; 4,496,654; 5,001,049; 5,075,078; 5,126,241; 5,120,643; 5,451,504; 5,424,193; 5,712,172; 6,555,390; 6,258,548; 6,699,722; 6,368,876 and 7,517,699; EP 0810436; EP 0296724; WO 92/12428; WO 94/01775; WO 95/16207; WO 97/06439; WO 98/36278; and WO 08/030546, each of which is incorporated by reference. Further, there are a number of commercially available lateral flow type tests and patents disclosing methods for the detection of large analytes (MW greater than 1,000 Daltons). U.S. Pat. No. 5,229,073 describes a semiquantitative competitive immunoassay lateral flow method for measuring plasma lipoprotein levels. This method utilizes a plurality of capture zones or lines containing immobilized antibodies to bind both the labeled and free lipoprotein to give a semi-quantitative result. In addition, U.S. Pat. No. 5,591,645 provides a chromatographic test strip with at least two portions. The first portion includes a movable tracer and the second portion includes an immobilized binder capable of binding to the analyte.

Many lateral flow devices are one-step lateral flow assays in which a biological fluid is placed in a sample area on a bibulous strip (though non-bibulous materials can be used, and rendered bibulous, e.g., by applying a surfactant to the material), and allowed to migrate along the strip until the liquid comes into contact with a specific binding partner (such as an antibody) that interacts with an analyte (such as one or more molecules) in the liquid. Once the analyte interacts with the binding partner, a signal (such as a fluorescent or otherwise visible dye) indicates that the interaction has occurred. Multiple discrete binding partners (such as antibodies) can be placed on the strip (for example in parallel lines) to detect multiple analytes (such as two or more molecules) in the liquid. The test strips can also incorporate control indicators, which provide a signal that the test has adequately been performed, even if a positive signal indicating the presence (or absence) of an analyte is not seen on the strip.

The construction and design of lateral flow devices is very well known in the art, as described, for example, in Millipore Corporation, *A Short Guide Developing Immunochromatographic Test Strips,* 2nd Edition, pp. 1-40, 1999, available by request at (800) 645-5476; and Schleicher & Schuell, *Easy to Work with BioScience, Products and Protocols* 2003, pp. 73-98, 2003, 2003, available by request at Schleicher & Schuell BioScience, Inc., 10 Optical Avenue, Keene, N. H. 03431, (603) 352-3810; both of which are incorporated herein by reference.

Lateral flow devices have a wide variety of physical formats that are equally well known in the art. Any physical format that supports and/or houses the basic components of a lateral flow device in the proper function relationship is contemplated by this disclosure.

In some embodiments, the lateral flow strip is divided into a proximal sample application pad, an intermediate test result zone, and a distal absorbent pad. The flow strip is interrupted by a conjugate pad that contains labeled conjugate (such as gold- or latex-conjugated antibody specific for the target analyte or an analyte analog). A flow path along strip passes from proximal pad, through conjugate pad, into test result zone, for eventual collection in absorbent pad. Selective binding agents are positioned on a proximal test line in the test result membrane. A control line is provided in test result zone, slightly distal to the test line. For example, in a competitive assay, the binding agent in the test line specifically binds the target analyte, while the control line less specifically binds the target analyte.

In operation of the particular embodiment of a lateral flow device, a fluid sample containing an analyte of interest, such as one or more molecules described herein (for example, protein antigens listed in Table 1, as discussed above), is applied to the sample pad. In some examples, the sample may be applied to the sample pad by dipping the end of the device containing the sample pad into the sample (such as serum or urine) or by applying the sample directly onto the sample pad (for example by placing the sample pad in the mouth of the subject). In other examples where a sample is whole blood, an optional developer fluid is added to the blood sample to cause hemolysis of the red blood cells and, in some cases, to make an appropriate dilution of the whole blood sample.

From the sample pad, the sample passes, for instance by capillary action, to the conjugate pad. In the conjugate pad, the analyte of interest, such as a protein of interest, may bind (or be bound by) a mobilized or mobilizable detector reagent, such as an antibody (such as antibody that recognizes one or more of the molecules described herein). For example, a protein analyte may bind to a labeled (e.g., gold-conjugated or colored latex particle-conjugated) antibody contained in the conjugate pad. The analyte complexed with the detector reagent may subsequently flow to the test result zone where the complex may further interact with an analyte-specific binding partner (such as an antibody that binds a particular protein, an anti-hapten antibody, or streptavidin), which is immobilized at the proximal test line. In some examples, a protein complexed with a detector reagent (such as gold-conjugated antibody) may further bind to unlabeled, oxidized antibodies immobilized at the proximal test line. The formation of a complex, which results from the accumulation of the label (e.g., gold or colored latex) in the localized region of the proximal test line is detected. The control line may contain an immobilized, detector-reagent-specific binding partner, which can bind the detector reagent in the presence or absence of the analyte. Such binding at the control line indicates proper performance of the test, even in the absence of the analyte of interest. The test results may be visualized directly, or may measured using a reader (such as a scanner). The reader device may detect color or fluorescence from the readout area (for example, the test line and/or control line).

In another embodiment of a lateral flow device, there may be a second (or third, fourth, or more) test line located parallel or perpendicular (or in any other spatial relationship) to test line in test result zone. The operation of this particular embodiment is similar to that described in the immediately preceding paragraph with the additional considerations that (i) a second detector reagent specific for a second analyte, such as another antibody, may also be contained in the conjugate pad, and (ii) the second test line will contain a second specific binding partner having affinity for a second analyte, such as a second protein in the sample. Similarly, if a third (or more) test line is included, the test line will contain a third (or more) specific binding partner having affinity for a third (or more) analyte.

1. Sample Pad

The sample pad is a component of a lateral flow device that initially receives the sample, and may serve to remove particulates from the sample. Among the various materials that may be used to construct a sample pad (such as glass fiber, woven fibers, screen, non-woven fibers, cellosic fibers or paper), a cellulose sample pad may be beneficial if a large bed volume (e.g., 250 µl/cm$^2$) is a factor in a particular application. Sample pads may be treated with one or more release agents, such as buffers, salts, proteins, detergents, and surfactants. Such release agents may be useful, for example, to promote resolubilization of conjugate-pad constituents, and to block non-specific binding sites in other components of a lateral flow device, such as a nitrocellulose membrane. Representative release agents include, for example, trehalose or glucose (1%-5%), PVP or PVA (0.5%-2%), Tween 20 or Triton X-100 (0.1%-1%), casein (1%-2%), SDS (0.02%-5%), and PEG (0.02%-5%).

2. Membrane and Application Solution:

The types of membranes useful in a lateral flow device (such as nitrocellulose (including pure nitrocellulose and modified nitrocellulose), nitrocellulose direct cast on polyester support, polyvinylidene fluoride, or nylon), and considerations for applying a capture reagent to such membranes have been discussed previously.

In some embodiments, membranes comprising nitrocellulose are preferably in the form of sheets or strips. The thickness of such sheets or strips may vary within wide limits, for example, from about 0.01 to 0.5 mm, from about 0.02 to 0.45 mm, from about 0.05 to 0.3 mm, from about 0.075 to 0.25 mm, from about 0.1 to 0.2 mm, or from about 0.11 to 0.15 mm. The pore size of such sheets or strips may similarly vary within wide limits, for example from about 0.025 to 15 microns, or more specifically from about 0.1 to 3 microns; however, pore size is not intended to be a limiting factor in selection of the solid support. The flow rate of a solid support, where applicable, can also vary within wide limits, for example from about 12.5 to 90 sec/cm (i.e., 50 to 300 sec/4 cm), about 22.5 to 62.5 sec/cm (i.e., 90 to 250 sec/4 cm), about 25 to 62.5 sec/cm (i.e., 100 to 250 sec/4 cm), about 37.5 to 62.5 sec/cm (i.e., 150 to 250 sec/4 cm), or about 50 to 62.5 sec/cm (i.e., 200 to 250 sec/4 cm). In specific embodiments of devices described herein, the flow rate is about 62.5 sec/cm (i.e., 250 sec/4 cm). In other specific embodiments of devices described herein, the flow rate is about 37.5 sec/cm (i.e., 150 sec/4 cm).

3. Conjugate Pad

The conjugate pad serves to, among other things, hold a detector reagent. Suitable materials for the conjugate pad include glass fiber, polyester, paper, or surface modified polypropylene. In some embodiments, a detector reagent may be applied externally, for example, from a developer bottle, in which case a lateral flow device need not contain a conjugate pad (see, for example, U.S. Pat. No. 4,740,468).

Detector reagent(s) contained in a conjugate pad is typically released into solution upon application of the test sample. A conjugate pad may be treated with various substances to influence release of the detector reagent into solution. For example, the conjugate pad may be treated with PVA or PVP (0.5% to 2%) and/or Triton X-100 (0.5%). Other release agents include, without limitation, hydroxypropylmethyl cellulose, SDS, Brij and β-lactose. A mixture of two or more release agents may be used in any given application. In a particular disclosed embodiment, the detector reagent in conjugate pad is a gold-conjugated antibody.

4. Absorbent Pad

The use of an absorbent pad in a lateral flow device is optional. The absorbent pad acts to increase the total volume of sample that enters the device. This increased volume can be useful, for example, to wash away unbound analyte from the membrane. Any of a variety of materials is useful to prepare an absorbent pad, for example, cellulosic filters or paper. In some device embodiments, an absorbent pad can be paper (i.e., cellulosic fibers). One of skill in the art may select a paper absorbent pad on the basis of, for example, its thickness, compressibility, manufacturability, and uniformity of bed volume. The volume uptake of an absorbent made may be adjusted by changing the dimensions (usually the length) of an absorbent pad.

The disclosure is illustrated by the following non-limiting Example.

EXAMPLE

In vivo Microbial Antigen Discovery of Antigens Method

This example provides an in vivo Microbial Antigen Discovery (InMAD) for identification of B. pseudomallei antigens that are shed into body fluids during infection. Antigens discovered in this manner are targets for immunoassays for diagnosis of B. pseudomallei associated conditions.

Figure 1:
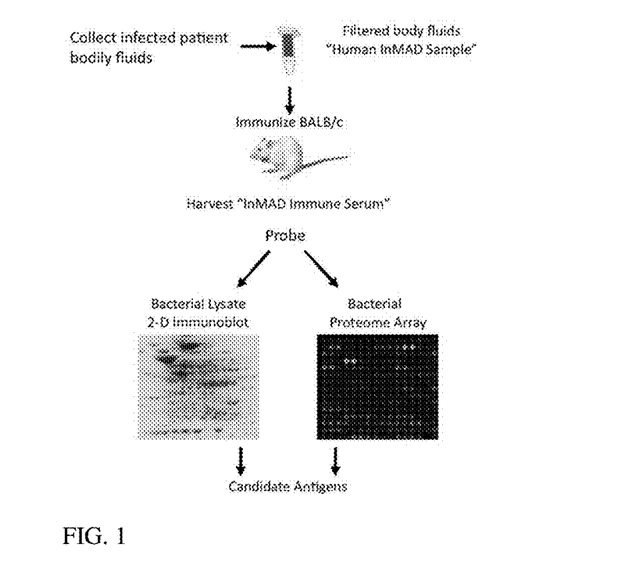
FIG. 1 is a schematic illustration of an exemplary InMAD strategy for identification of targets for immunoassay by using human biological samples.
Figure 2A:
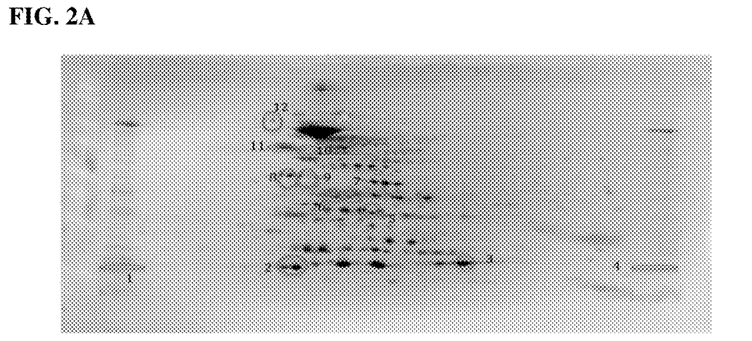
FIG. 2A is a digital image of a two-dimensional blot of *Burkholderia pseudomallei* lysate probed with InMAD immune serum illustrating the total proteins from the *Burkholderia pseudomallei*.
Figure 2B:
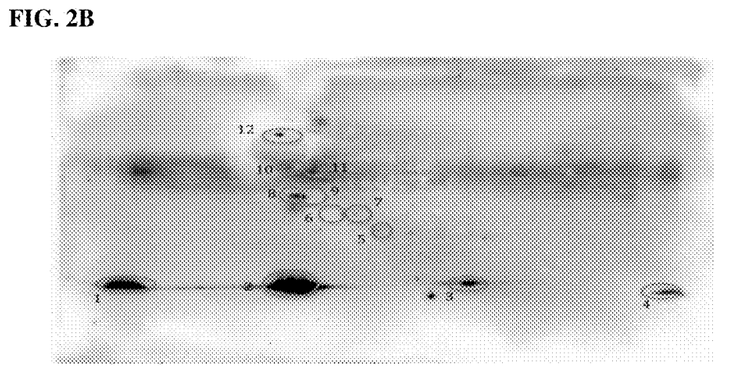

FIG. 1 provides a schematic of InMAD